United States Patent [19]

Le Disert et al.

[11] Patent Number: 5,348,578
[45] Date of Patent: Sep. 20, 1994

[54] PRODUCTS OBTAINED FROM THE REACTION OF AMINE-DIOL AND A POLYFUNCTIONAL SUBSTANCE AND APPLICATION OF SUCH PRODUCTS TO ELECTROAPPLICABLE CATIONIC PAINT COMPOSITIONS

[75] Inventors: Yves Le Disert, Drancy; Jean Roue, Bussy Saint Georges, both of France; Thomas Moriarity, Wexford, Pa.; Philippe Faucher, Paris, France

[73] Assignee: PPG Industries (France) S.A., Valenciennes Cedex, France

[21] Appl. No.: 78,229

[22] PCT Filed: Oct. 21, 1992

[86] PCT No.: PCT/FR92/00988

§ 371 Date: Jun. 23, 1993

§ 102e Date: Jun. 23, 1993

[87] PCT Pub. No.: WO93/08157

PCT Pub. Date: Apr. 29, 1993

[30] Foreign Application Priority Data

Oct. 23, 1991 [FR] France .................... 91 13118

[51] Int. Cl.$^5$ ............................ C09D 175/08
[52] U.S. Cl. ...................... 106/287.2; 106/14.05; 106/14.15; 106/14.16; 106/287.23; 106/287.25; 106/499; 106/506
[58] Field of Search ............. 106/499, 506, 14.05, 106/14.15, 14.16, 287.2, 287.23, 287.25

[56] References Cited

U.S. PATENT DOCUMENTS

| | | | |
|---|---|---|---|
| 3,947,338 | 3/1976 | Jerabek et al. | 204/181 |
| 4,001,329 | 1/1977 | Bell | 564/326 |
| 4,031,050 | 6/1977 | Jerabek | 523/415 |
| 4,281,196 | 7/1981 | Rutzen et al. | 564/292 |
| 4,588,840 | 5/1986 | Gurgiolo | 564/443 |
| 4,689,131 | 8/1987 | Roue et al. | 204/181.7 |
| 4,761,502 | 8/1988 | Kluger et al. | 564/442 |
| 4,810,535 | 3/1989 | McCollum et al. | 427/410 |

FOREIGN PATENT DOCUMENTS 193685 9/1986 European Pat. Off. .
2187449 9/1987 United Kingdom .

OTHER PUBLICATIONS

Chemical Abstracts, vol. 101, No. 24, 10 Dec. 1984, Abstract No. 215560x, D. Brodrecht et al, "Cationic Emulsion for Road Construction".
Chemical Abstracts, vol. 104, No. 21, 26 May 1986, Abstract No. 185507c, B. Keil et al, "Soil Stabilizers".
Chemical Abstracts, vol. 97, No. 22, 29 Nov. 1982, Abstract No. 184144g, Canon, K.K. "Jet Printing Inks".
Chemical Abstracts, vol. 79, No. 26, 31 Dec. 1973, Abstract No. 151696p, Maeda, S., "Desensitizer Compositions for Pressure-Sensitive Copying Paper".

Primary Examiner—Mark L. Bell
Assistant Examiner—Scott L. Hertzog
Attorney, Agent, or Firm—William J. Uhl

[57] ABSTRACT

Product obtained from the reaction of
(a) an amine-diol resulting from the reaction of a primary amine having the formula R-NH$_2$ in which R represents an aliphatic or aromatic radical, with at least one alkylene oxide comprising predominantly propylene oxide, and
(b) at least one polyfunctional substance, capable of acting on the hydroxyl groups of said amine-diol.

The product disclosed may be used as an additive in an electrodeposition paint composition in order to furnish, after application to a metal substrate, a coating or film having an improved resistance to pinholes and to cratering.

16 Claims, No Drawings

PRODUCTS OBTAINED FROM THE REACTION OF AMINE-DIOL AND A POLYFUNCTIONAL SUBSTANCE AND APPLICATION OF SUCH PRODUCTS TO ELECTROAPPLICABLE CATIONIC PAINT COMPOSITIONS

FIELD OF THE INVENTION

The present invention concerns the field of electroapplicable paints. Its object is products obtained from the reaction of an amine-diol with a polyfunctional substance, said products having the character of a resin. Through the introduction of cationic groups, said resin can be put in the form of an aqueous dispersion which can be employed directly as an additive in an electroapplicable cationic paint composition.

PRIOR ART

The technique for forming a paint or varnish by electrodeposition from a bath of suitable chemical composition is known to a person skilled in the art. There are many bibliographic and patent references on such a subject. Illustrations in the field of the invention are provided by U.S. Pat. Nos. 4,689,131 and 4,810,535, which were recently granted, and which describe additives intended to improve the appearance of coatings obtained by electrodeposition. Such a technique finds wide application in the automotive industry. In fact, vehicle bodies are routinely coated with a paint or a varnish by electrodeposition.

At the present time, there is an intensified search for sheet metal which has good corrosion resistance, and this leads to the selection of special ferrous alloys and of enamel compositions which are further improved in comparison with those already available. For example, it has been found that iron/zinc alloys are suitable for the production of sheet metal having good corrosion resistance. It is known, nevertheless, that this type of sheet metal, in particular, is difficult to treat by the electrodeposition technique if the end purpose is to produce a flawless surface coating. In particular, the appearance of pinholes or craters is observed, these being surface defects caused by the application of the potential difference needed for the electrodeposition (or electrophoresis). When sheet metal components, as in the case of vehicle car bodies, have areas that are accessible with difficulty, there is a tendency to increase the voltage applied to make certain that the whole of the body will be provided with a suitable coating. By this very fact, the risk of pinholes is increased, these being, in fact, attributable to small electric arcs initiated at the metal substrate and passing through the surface coating.

The presence of a perfectly continuous electrophoretic coating is obviously eminently desirable, not only for corrosion resistance but also for a property commonly known as 'gravel impact resistance', which reflects the ability of the metal parts of the vehicle to withstand the impact of a wide variety of objects, to which these areas may be subjected when the vehicle is used.

Compounds of the amine-diol type are known in the prior art. Such compounds have already been used, for example, to impregnate fabrics to give them gloss. This application was the subject of patent application EP-79.103.847 (Publication No.EP-11.130). The products described in this document are low-polymerized amine-diols.

U.S. Pat. No. 4,001,329 concerns a product obtained from the reaction between an aniline, formaldehyde and diethanolamine. The product is used for the production of polyurethane foam. The compound obtained is a polyol containing free hydroxyl groups.

U.S. Pat. No. 4,761,502 also concerns the preparation of amine-diols of which the hydroxyl groups are not substituted. The products are used as intermediates in the manufacture of dyes.

Other applications of amines substituted by aliphatic or aromatic groups are also described in the literature. Compounds of this type have been used to improve the performance of printing inks (Chemical Abstracts, Vol.97, No.22, 1982, abstract No.184.144.G), in the manufacture of pressure-sensitive copying paper (Chemical Abstracts, Vol.79, No.25, 1973, abstract No.151.696.P), and in cationic emulsions used as soil stabilizers (Chemical Abstracts, Vol.101, No.24, 1984, abstract No.215.560.X, and Chemical Abstracts, Vol.104, No.21, 1986, abstract No.185.507.C).

However, the products described in the prior art only have low molecular weights, and have not been used to prepare, by reaction with other active agents, additives for paint compositions.

GENERAL DESCRIPTION OF THE INVENTION

The object of the invention is an additive which can be used in an electroapplicable paint composition which, after application to a metal substrate, yields a coating or film having an improved resistance to pinholes and to cratering.

Another object of the invention is to provide an additive of the above type, which improves the film appearance in an electroapplicable cationic paint system, and which simultaneously does not impair the adhesiveness of the layers usually applied to coat sheet metal, such as finishing coats or body compounds.

Yet another object of the invention is to provide an additive for an electroapplicable paint, whose composition makes it possible to work with higher potential differences, offering a better opportunity to coat the less accessible areas of a metal substrate, such as a vehicle body.

Yet another object of the invention is an additive for an electroapplicable cationic paint system which, in many cases, does not use solvents, and this contributes to the protection of the environment, since the electrodeposition can be carried out without the need to observe the precautions that are indispensable with systems that include a solvent.

In its general form, the invention concerns the product obtained from the reaction of an amine-diol, such as defined hereafter, and a polyfunctional substance which is capable of reacting with the hydroxyl groups of said amine-diol.

The amine-diol used to prepare the product of the invention is itself obtained from the reaction of a primary amine having the formula $R-NH_2$, in which R represents an aliphatic or aromatic radical, with at least one alkylene oxide comprising predominantly propylene oxide.

With a view to its use in electroapplicable paint systems, it is caused to react with at least one polyfunctional substance capable of acting on its hydroxyl groups, in order to form a resin.

The R group of the amine generally contains 1 to 20 carbon atoms. It is preferably an alkyl or aralkyl group, with a linear or branched chain. Preference is given to amines in which the R radical contains from 1 to 12 carbon atoms and is chosen, for example, from methyl, butyl or lauryl radicals. The R group may also be of the aromatic type, for example a phenyl group. In this case it may contain 6 to 18 carbon atoms, with preference given to the range from about $C_6$ to $C_{12}$.

The other reactant used to prepare the amine-diol of the invention is an alkylene oxide comprising predominantly propylene oxide. This expression means that, for the needs of the invention, that is to say in the use of electroapplicable paint systems, ethylene oxide, used alone in reaction with the amine $R\text{-}NH_2$ would not be suitable, because it would give rise to a compound having excessively high solubility properties. This is why it is most advantageous to use propylene oxide. However, the latter can be used in a mixture with other alkylene oxides, even with a small proportion of ethylene oxide. Butylene oxide or isobutylene oxide can be used in theory, but, in this case, it is preferable to mix them with propylene oxide. For the invention, the latter is present predominantly, that is to say in a proportion of more than 50% by weight, and preferably more than 80% by weight with respect to the mixture of alkylene oxides.

DESCRIPTION OF THE PREFERRED EMBODIMENT

According to a preferred embodiment of the invention, it was found that the compound of the amine-diol type should have a molecular weight ranging approximately between 800 and 1500 and, even better, between 1000 and 1200. Practical tests have in fact demonstrated that additives obtained from amine-diol with a molecular weight higher than approximately 1500, for example in the range of 2000, while offering very good resistance to cratering, cause a deterioration of the adhesiveness of certain finishing coats (especially those based on alkyd resins). Moreover, the products resulting from an amine-diol having a molecular weight lower than 800, approximately from 500 to 800 for example, do not exhibit any adhesion defects, but do not offer good resistance to cratering. According to the invention, it was accordingly found that, to provide for an additive offering good adhesion qualities and simultaneously good resistance to cratering, the appropriate molecular weight ranges of the amine-diol are approximately between 800 and 1500 and, even better, between 1000 and 1200.

In the first step, the reaction of the primary amine $R\text{-}NH_2$ with the alkylene oxide is carried out in order to place the two components of the reaction in contact under mild conditions, that is to say without catalyst and with a moderate rise in temperature (not exceeding 50° C., the reaction temperature then being, for example, 40° C.), and with a slight excess of amine with respect to alkylene oxide. This excess can be up to 2/1 on a molar basis.

The reaction is then continued to extend the chain of the compound by placing additional alkylene oxide molecules in contact with the product resulting from the first step, and in the presence of a basic catalyst, such as potassium hydroxide. The reaction is continued until the molecular weight has been adjusted within the ranges indicated above.

The formation of the amine-diol by reaction of the amine $R\text{-}NH_2$ with an alkylene oxide O-Alk was first illustrated schematically as follows:

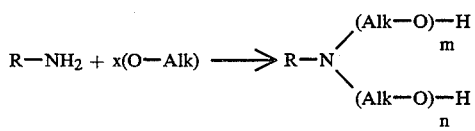

with m+n=x.

The reaction mechanism in the case of propylene oxide is also illustrated below. The reaction mechanism was simplified to show the reaction of x moles of propylene oxide until the amine-diol compound with the desired molecular weight was obtained:

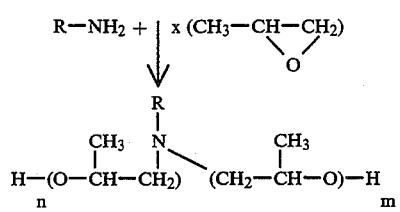

with m+n=x.

The amine-diol thus obtained, which is a tertiary mono-amine, contains hydroxyl groups. A person skilled in the art will understand that the number of alkylene oxide links, in particular propylene oxide, will vary according to the molecular weight to be obtained, and also in accordance with the basic amine $R\text{-}NH_2$ employed. In general, the number of propylene oxide groups can vary from 10 to 40.

With a view to its use in electroapplicable paint systems, the amine-diol type of compound is caused to react, to form a resin, with at least one polyfunctional substance capable of acting on the hydroxyl groups of the amine-diol. There are many substances capable of performing this function, the most accessible ones being isocyanates, acids and acid anhydrides. The result of such a reaction is an extension of the chain and an increase in the molecular weight, culminating in a resin which, by neutralization, is capable of forming an aqueous dispersion by virtue of the formation of cationic sites.

Use is advantageously made of diisocyanates such as toluene diisocyanate, isophorone diisocyanate, hexamethylene diisocyanate, tetramethylphenyl isocyanate, methylenediphenyl diisocyanate (MDI) and polymethylene polyphenyl isocyanate and other similar isocyanates already known in the technique of electroapplicable resins. On this subject, reference can be made to U.S. Pat. No. 4,689,131, already mentioned at the beginning of this description. The reaction conditions involve the use of excess amine-diol with respect to the isocyanate. If the proportions of reactants are defined by the equivalents of OH groups with respect to the NCO isocyanate groups, the molar ratio OH/NCO may range approximately between 2/1 and 4/3, a ratio close to 3/2 being preferred.

As indicated above, instead of isocyanates, use can be made of other chain extenders, such as acids and acid anhydrides, particularly diacids or diacid anhydrides, such as phthalic or maleic acids or anhydrides.

The proportions of the amine-diols with respect to the acids or acid anhydrides will range advantageously between 2/3 and 4/3, with a preference for 3/2, said ratio being defined as the equivalents of OH groups with respect to the $CO_2H$ groups ($OH/CO_2H$ in moles).

However, in practice, however, preference is assigned to isocyanates, because the reaction times with acids and acid anhydrides are generally longer.

In certain cases, and particularly if the R radical of the amine $R-NH_2$ contains more than 1 or 2 carbon atoms, it may be necessary, to ensure a good aqueous dispersion of the resin prepared from the corresponding amine-diol compound, to use jointly, as is known to a person skilled in the art, another resin, known as a milling resin, which facilitates dilution in water. This technique is known per se and is illustrated in the examples that follow.

The invention thus provides an additive preventing the formation of craters, exhibiting excellent adhesiveness to the primers, body compounds and finishing coats, and also imparting improved resistance of the film to the formation of pinholes on metal substrates, particularly on metal substrates based on heterogeneous alloys, more specifically of the iron/zinc type, and particularly substrates pretreated by galvanizing, zinc electroplating or, more generally, by the deposition of a zinc coating. In addition, the product of the invention comprises a solvent-free polymer.

The invention is illustrated further, without being limited in any manner, by the examples below.

Unless otherwise indicated, all the parts are expressed by weight.

EXAMPLE 1

A pigment grinding vehicle is prepared from a mixture of the following constituents.

| ingredient | parts by weight | solids | equivalents |
| --- | --- | --- | --- |
| Epon 828* | 531.00 | 531.0 | 2.82 |
| bisphenol A | 208.00 | 208.0 | 1.82 |
| triethylphenylphosphonium iodide | 0.53 | | |
| xylene | 19.10 | | |
| 2-ethylhexanolmonourethane of 2,4-toluene diisocyanate, 95% in methylisobutylketone | 301.40 | 286.3 | |
| quaternizing agent (1) | 461.30 | 315.9 | |
| 2-butoxyethanol | 1001.90 | | |
| | 2523.20 | 1341.2 | |

*Epoxy resin obtained from the reaction of epichlorhydrin with bisphenol A, which as an epoxy equivalent of 188, marketed by Shell Chemical Company.
(1) The quaternizing agent is prepared by causing 328 parts by weight of 2-ethylhexanolmonourethane to react with 2,4-toluene diisocyanate in methylethylketone at ambient temperature, with 9.2 parts by weight of trimethylethanolamine. The mixture is left to exothermic reaction and held for 1 h at 80° C., and then 120.3 parts by weight of lactic acid are added, followed by 107 parts of butoxyethanol. The reaction mixture is then stirred for 1 h at 65° C., after the incorporati on of 94 parts by weight of water.

The catalyst, xylene, Epon 828 and bisphenol A were introduced under nitrogen atmosphere into a reactor and heated to between 150° and 160° C. to initiate the exothermic reaction. After 1 h at 160° C., the reaction mixture was cooled to 120° C. and the 2-ethylhexanolmonourethane of 2,4-toluene diisocyanate, at 95% in methylisobutylketone, was added. The temperature of the reaction mixture was held at 115° C. for 1 h, and the 2-butoxyethanol was then added. The reaction mixture was then cooled to 85° C., homogenized, and the quaternizing agent then added. The temperature of the reaction mixture was held at 80° to 85° C. until an acid number of about 1 was obtained. The reaction mixture had a solids content of 53%.

EXAMPLE 2

A conventional cationic resin was prepared from the following mixture of ingredients.

| ingredient | parts by weight | solids | equivalents |
| --- | --- | --- | --- |
| Epon 828 | 702.2 | 702.2 | 3.735 |
| PCP 200** | 263.4 | 263.4 | 1.000 |
| bisphenol A | 197.8 | 197.8 | 1.735 |
| xylene | 61.6 | | |
| benzyldimethylamine | 3.8 | | |
| capped isocyanate cross-linking agent (2) | 891.0 | 629.1 | |
| diketimine derived from diethylenetriamine and methylisobutylketone (76% solids content in methylisobutylketone) | 75.3 | 54.7 | 0.612 |
| N-methylethanolamine | 59.1 | 59.1 | 0.787 |
| phenoxypropanol | 126.9 | 11.7 | |
| cationic surfactant (3) | 29.3 | 11.7 | |
| acetic acid | 29.5 | | |
| $H_2O$ 36% | 2917.2 | | |
| | 5327.8 | 1918.0 | |

**PCP 200: polycaprolactonediol sold by Union Carbide Corporation.
(2) Polyurethane cross-linking agent, obtained from the reaction of toluene diisocyanate (80/20 mixture of 2,4/2,6 isomers), with 2-ethylhexanol, and treatment of the product with trimethylolpropane in a molar proportion of 3/1. The cross-linking agent is present in the form of a solution in methoxypropanol with a solids content of 70%.
(3) The cationic surfactant is prepared by blending 120 parts of an alkylimidazoline marketed by Geigy Industrial Chemical under the name Geigy Amine C, 120 parts by weight of an acetylenic alcohol marketed by Ast Products and Chemicals Inc under the name Surfynol 104, 120 parts by weight of 2-butoxyethanol, 221 parts by weight of deionized water, and 19 parts by weight of glacial acetic acid.

The Epon 828, PCP 200 and xylene were introduced into a reactor and heated to 210° C. with nitrogen sparging. The reaction mixture was kept under reflux for ½ h to remove the water. The reaction mixture was cooled to 150° C., and the bisphenol A and 1.6 parts of the benzyldimethylamine catalyst were added. The reaction mixture was heated to 150° to 190° C. and kept at this temperature for about 1½ h, and then cooled to 130° C. The remainder of the benzyldimethylamine catalyst was added, and the reaction mixture kept at 130° C. for about 3 h, until a reduced viscosity was obtained (solution with a 50% resin solids content in methoxypropanol), corresponding to the value P on the Gardner-Holdt scale.

The polyurethane cross-linking agent, diketimine and methylethanolamine were then introduced, and the temperature of the reaction mixture was raised to 110° C. and kept at this value for 1 h.

The phenoxypropanol was added, and the reaction mixture dispersed in water after having been added to a mixture of acetic acid, deionized water and cationic surfactant (3). This dispersion was diluted to 36% solids content with deionized water.

EXAMPLE 3

A conventional cationic resin stripped of solvents by distillation was prepared from the following mixture of ingredients.

| ingredient | parts by weight | solids | equivalents |
| --- | --- | --- | --- |
| Epon 828 | 682.3 | 682.3 | 3.629 |
| bisphenol A | 197.7 | 197.7 | 1.732 |
| polyetherdiol (1) | 238.7 | 238.7 | 1.000 |
| methylisobutylketone | 58.8 | | |
| benzyldimethylamine (total) | 2.3 | | |
| polyurethane cross-linking | 975.4 | 682.8 | |

-continued

| ingredient | parts by weight | solids | equivalents |
|---|---|---|---|
| agent (2) |  |  |  |
| diketimine derived from diethylenetriamine and methylisobutylketone (76% solids content in methylisobutylketone) | 76.1 | 55.5 |  |
| N-methylethanolamine | 64.8 | 64.8 |  |
| phenoxypropanol | 96.2 |  |  |
| lactic acid | 70.0 | 61.6 |  |
| H₂O | 3548.0 |  |  |
|  | 6010.3 | 1983.4 |  |

(1) Diol obtained from the reaction of bisphenol A with ethylene oxide with a stoichmetry such that the final product has a hydroxyl equivalent weight of approximately 239.
(2) Polyurethane cross-linking agent obtained from toluene diisocyanate (80/20 mixture of 2,4/2,6 isomers) with hexoxyethanol (ethylene glycol monohexyl ether), diluted to 70% in methylisobutylketone.

The Epon 828, polyetherdiol, bisphenol A and methylisobutylketone were introduced into a reactor and heated to 200° C. with nitrogen sparging. The reaction mixture was kept under reflux for about ½ h to remove the water. The reaction mixture was cooled to 150° C., and 1.1 parts of benzyldimethylamine catalyst were added. The reaction mixture was heated to 150° to 190° C. and kept at this temperature for about 1 h, then cooled to 130° C. before adding 1.2 parts of benzyldimethylamine and holding for approximately 3 h until a reduced Gardner-Holdt viscosity corresponding to the value R was obtained (50% solids content in methoxypropanol).

The polyurethane cross-linking agent, diketamine and N-methylethanolamine were then introduced into the reaction mixture, and the temperature raised to 110° C. and kept at this value for 1 h.

The phenoxypropanol was added, and the reaction mixture was dispersed in water by addition to a mixture of lactic acid and deionized water. This dispersion was diluted with deionized water to a solids content of 33%, and was distilled under vacuum to remove the volatile organic solvents, in order to yield a dispersion with a solids content of 38%.

EXAMPLE 4

A methylaminopolyoxypropylenediol was prepared from the mixture of the following ingredients.

| ingredient | parts by weight | solids | equivalents |
|---|---|---|---|
| methylamine 40% in water | 77.5 | 31.0 | 1.000 |
| propylene oxide | 115.7 | 115.7 | 1.995 |
| KOH | 1.1 |  |  |
| propylene oxide | 866.2 | 866.2 | 13.935 |
| acetic acid | 1.1 |  |  |
|  | 1061.6 | 1012.9 |  |

The methylamine solution is introduced into a dry, clean reactor fitted with a stirrer, and provided with heating and cooling, and capable of maintaining an internal pressure of 1034 kPa (150 psi) under sealing, and the reactor is hermetically sealed. The temperature is raised to 40° C., and the propylene oxide is added slowly at this temperature. The exothermic reaction is controlled by cooling, and by the rate of addition of propylene oxide. The reaction temperature is then held at 40° C. When all the oxide has been introduced into the reactor, the reaction mixture is kept at 40° C. for 1 h, after which a sample is taken to determine the tertiary amine content and the neutralization equivalent (94% minimum and 180 to 200 respectively).

When the analyses for the tertiary amine and the neutralization equivalent are satisfactory, the reaction mixture is heated to 100° C., and the water is stripped by vacuum distillation under a pressure below 1333 Pa (10 mmHg). Removal by distillation is stopped when the water content, measured by the Karl Fischer method, is less than 0.15%.

When the water content is satisfactory, the reaction mixture is cooled to 40° C. and the KOH catalyst is added. The reactor is then purged with nitrogen (three times). The reaction mixture is then heated to 120° C., and propylene oxide is added slowly. The temperature is maintained at 120° to 125° C. by controlling the rate of addition of propylene oxide and by cooling the reactor. After all the oxide has been introduced, the reaction mixture is kept at 120° to 125° C. for 1 h, and samples are then taken to determine the neutralization equivalent and the tertiary amine content. If necessary, propylene oxide can be added and caused to react, to adjust the reaction.

Once the product is assessed and approved, it is cooled to 40° C. and neutralized with acetic acid.

| Neutralization equivalent | 1000 to 1250 |
|---|---|
| Tertiary amine | 94% minimum |
| Hydroxyl equivalent weight | 430 to 510 |

EXAMPLE 5

A laurylaminopolyoxypropylenediol was prepared from the following mixture of ingredients.

| ingredient | parts by weight | solids | equivalents |
|---|---|---|---|
| laurylamine | 171.0 | 171.0 | 1.000 |
| propylene oxide | 115.7 | 115.7 | 1.995 |
| KOH | 1.1 |  |  |
| propylene oxide | 866.2 | 866.2 | 14.935 |
| acetic acid | 1.1 |  |  |
|  | 1155.1 | 1152.9 |  |

The procedure is similar to the one described in Example 4, the neutralization equivalent and hydroxyl weight being adjusted.

EXAMPLE 6

A butylaminopolyoxypropylenediol was prepared from the following mixture of ingredients.

| ingredient | parts by weight | solids | equivalents |
|---|---|---|---|
| butylamine | 73.0 | 73.0 | 1.000 |
| propylene oxide | 115.7 | 115.7 | 1.995 |
| KOH | 1.1 |  |  |
| propylene oxide | 866.2 | 866.2 | 14.935 |
| acetic acid | 1.1 |  |  |
|  | 1057.1 | 1054.9 |  |

The procedure is similar to the one described in Example 4, the neutralization equivalent and the hydroxyl equivalent weight being adjusted.

EXAMPLE 7

A phenylaminopolyoxypropylenediol was prepared from the following mixture of ingredients.

| ingredient | parts by weight | solids | equivalents |
| --- | --- | --- | --- |
| phenylamine | 91.0 | 91.0 | 1.000 |
| propylene oxide | 115.7 | 115.7 | 1.995 |
| KOH | 1.1 | | |
| propylene oxide | 866.2 | 866.2 | 14.935 |
| acetic acid | 1.1 | | |
| | 1075.1 | 1072.9 | |

The procedure is similar to the one described in Example 4, the neutralization equivalent and hydroxyl equivalent weight being adjusted.

EXAMPLE 8

A polyurethanepolyaminodiol was prepared from the following mixture of ingredients.

| ingredient | parts by weight | solids | equivalents |
| --- | --- | --- | --- |
| methylaminopolyoxypropylene-diol from Example 4 | 2712.0 | 2712 | 6 (OH) |
| MIBK (methylisobutylketone) | 135.6 | | |
| dibutyltin dilaurate | 0.5 | | |
| toluene diisocyanate (80/20, 2,4/2,6 isomers) | 348.0 | 348.0 | 4 (NCO) |
| acetic acid | 180.0 | | 3.0 |
| deionized water | 5123.9 | | |
| | 8500.0 | 3600 | |

The methylaminopolyoxypropylenediol and methylisobutylketone were introduced into a reactor under nitrogen blanket and heated to 120° C. At 120° C., the reaction mixture is placed under vacuum to remove the methylisobutylketone and to dry the amine-diol. When the distillation is completed, the vacuum inlet is stopped with the help of a nitrogen blanket, and the temperature is lowered to 60° C.

At 60° C., the catalyst is added, and the addition of toluene diisocyanate is started. The exothermic reaction is thermostatically controlled (by the rate of addition of the toluene diisocyanate and by cooking) at a maximum temperature of 80° C. When the addition is completed, the product is held at 80° C. for 1 h, until no NCO group can be detected by infrared.

The product is then dissolved in a mixture of acetic acid and deionized water.

EXAMPLE 9

A polyurethanepolyaminodiol was prepared from the following mixture of ingredients.

| ingredient | parts by weight | solids | equivalents |
| --- | --- | --- | --- |
| methylaminopolyoxypropylene-diol from Example 4 | 2712.0 | 2712 | |
| MIBK (methylisobutylketone) | 135.6 | | |
| dibutyltin dilaurate | 0.5 | | |
| toluene diisocyanate (80/20, 2,4/2,6 isomers) | 348.0 | 348 | |
| grinding vehicle for Example 1 | 6018.0 | 3190 | |
| acetic acid | 130.0 | | |
| deionized water | 8153.0 | | |
| | | 6250 | |

The procedure is the same as in Example 8, except that the mixture also includes the grinding vehicle from Example 1.

For this purpose, the product is mixed with acetic acid and said grinding vehicle, and finally dispersed in deionized water.

EXAMPLE 10

A polyurethanepolyaminodiol was prepared from the following mixture of ingredients.

| ingredient | parts by weight | solids | equivalents |
| --- | --- | --- | --- |
| laurylaminopolyoxypropylenediol from Example 5 | 3060.0 | 3060 | 6 (OH) |
| MIBK (methylisobutylketone) | 153.0 | | |
| dibutyltin dilaurate | 0.5 | | |
| toluene diisocyanate (80/20, 2,4/2,6 isomers) | 348.0 | 348 | 4 (NCO) |
| acetic acid | 165.0 | | 2.75 |
| grinding vehicle from Example 1 | 6430.0 | 3408 | |
| H$_2$O for 36% solids content | 8930.0 | | |
| | 18933.0 | 6816 | |

The procedure is similar to the one described in Example 9.

EXAMPLE 11

A polyurethanepolyaminodiol was prepared from the following mixture of ingredients.

| ingredient | parts by weight | solids | equivalents |
| --- | --- | --- | --- |
| butylaminopolyoxypropylenediol from Example 6 | 3114.0 | 3114 | 6 (OH) |
| methylisobutylketone | 155.7 | | |
| dibutyltin dilaurate | 0.5 | | |
| toluene diisocyanate (80/20, 2,4/2,6 isomers) | 348.0 | 348 | 4 (NCO) |
| acetic acid | 148.0 | | |
| grinding vehicle from Example 1 | 6811.0 | 3610 | |
| deionized water | 9223.0 | | |
| | 19644.0 | 7072 | |

The procedure is similar to the one described in Example 9.

EXAMPLE 12

A polyurethanepolyaminodiol was prepared from the following mixture of ingredients.

| ingredient | parts by weight | solids | equivalents |
| --- | --- | --- | --- |
| phenylaminopolyoxypropylene-diol from Example 7 | 3468.0 | 3468.0 | |
| (OH)methylisobutylketone | 173.4 | | |
| dibutyltin dilaurate | 0.5 | | |
| toluene diisocyanate (80/20, 2,4/2,6 isomers) | 300.6 | 300.6 | 3.45 (NCO) |
| acetic acid | 123.0 | | 2.06 |
| grinding vehicle from Example 1 | 7343.0 | 3821.6 | |
| deionized water | 10385.4 | | |
| | 21793.9 | 7590.2 | |

The procedure is similar to the one described in Example 9.

EXAMPLE 13 (comparison)

A polyoxyalkylenepolyaminepolyepoxide addition product as described in Example 1 of U.S. Pat. No. 4,432,850 was prepared from the following mixture of ingredients.

| ingredient | parts by weight | solids | equivalents |
|---|---|---|---|
| Jeffamine D2000 (1) | 1415.9 | | |
| Epon 1001 (2) | 489.1 | | |
| 2-butoxyethanol | 179.8 | | |
| acetic acid | 29.5 | | |
| H$_2$O for 36% solids content | 3178.0 | | |
| | 5292.3 | | |

(1) Jeffamine D2000 is a polyoxypropylenediamine with a molecular weight of 2000, marketed by Jefferson Chemical Company or Texaco.
(2) Epon 101 is a polyglycidyl ether of bisphenol A having an epoxy equivalent of 523, available from Shell Chemical Company.

The Jeffamine D2000 was introduced into a reactor under nitrogen atmosphere and heated to 90° C., and a solution of Epon 1001 in butoxyethanol was then added. The reaction mixture was heated to 110° C. and held for 2 h. The reaction mixture was dispersed in acetic acid and deionized water.

EXAMPLE 14

A pigment paste was prepared from the following mixture of ingredients.

| ingredient | parts by weight | solids | equivalents |
|---|---|---|---|
| titanium dioxide | 44.42 | | 44.42 |
| lead silicate | 2.90 | | 2.90 |
| carbon black | 0.37 | | 0.37 |
| grinding vehicle from Example 1 | 18.50 | | 9.80 |
| deionized water | 27.51 | | |
| catalyst paste (1) | 6.30 | | 2.52 |
| | 100.00 | | 60.00 |

The above ingredients were ground in a mill to a Hegman No. 7 fineness.

Coating compositions that can be applied by cationic electrodeposition

Examples 15 to 24 below concern coating compositions that can be applied by cationic deposition, containing the new additives according to the invention, intended to improve the surface appearance without undesirably affecting the adhesiveness, and also concern additives for comparison.

The compositions were applied by cathodic electrodeposition on steel panels previously subjected to treatment with zinc phosphate. The electrodeposited coatings were cured at elevated temperature, and the surface appearance of the cured coatings was assessed. The electrodeposited and cured coatings were then coated with various alkyd and polyester coating compositions, and the topcoat was assessed for adhesiveness to the bottom coat obtained by electrodeposition. The thickness of the dry topcoat film was approximately 35 to 40 μm. Additive-free compositions were also evaluated for comparative purposes. The results of the tests are summarized in Table 1 below.

EXAMPLE 15

An additive-free cationic electrodeposition bath was prepared as a control by mixing the following ingredients.

| ingredient | parts by weight | solids | equivalents |
|---|---|---|---|
| resin for cationic electrodeposition from Example 2 | 988 | | |
| pigment paste from Example 14 | 157 | | |
| deionized water | 1855 | | |
| | 3000 | | |

Steel panels subjected to pretreatment with zinc phosphate were coated by cathodic electrophoresis in an electrodeposition bath at 200 V at a temperature of 24° C. The deposition time was calculated to give a film thickness of 20 to 23 μm after curing. In this example, the time was 3 min 40 s.

These panels were used to check the adhesiveness of the topcoat and the resistance to crater formation. In this case, before the panels were baked, drops of oil were placed with a syringe on the uncured electrodeposited film.

To evaluate the resistance of the film to the formation of craters in the absence of a severe contaminant, such as oil, an ACT type cold-rolled steel, marketed by Advanced Coating Technologies Inc, and having a very smooth surface, was coated in the resin bath.

EXAMPLE 16

An additive-free cationic electrodeposition bath was prepared as a control by mixing the following ingredients.

| ingredient | parts by weight | solids | equivalents |
|---|---|---|---|
| resin for cationic electrodeposition from Example 2 | 889 | | |
| pigment grinding vehicle resin from Example 1 | 68 | | |
| pigment paste from Example 14 | 157 | | |
| deionized water | 1188 | | |
| | 2302 | | |

The panels received a coating by electrophoresis as described in Example 15. The deposition time on steel panels subjected to pretreatment with zinc phosphate was 2 min 40 s.

EXAMPLE 17

A cationic electrodeposition bath containing the addition product from Example 9 was prepared by mixing the following ingredients.

| ingredient | parts by weight | solids | equivalents |
|---|---|---|---|
| resin for cationic electrodeposition from Example 2 | 790 | | |
| pigment paste from Example 14 | 15 | | |
| deionized water | 1855 | | |
| additive from Example 9 | 198 | | |
| | 3000 | | |

The panels received a coating by electrophoresis as described in Example 15. The deposition time on steel panels which had been subjected to pretreatment with zinc phosphate was 2 min 30 s.

EXAMPLE 18

A cationic electrodeposition bath containing the addition product from Example 10 was prepared by mixing the following ingredients.

| ingredient | parts by weight | solids | equivalents |
|---|---|---|---|
| resin for cationic electrodeposition from Example 2 | 790 | | |
| pigment paste from Example 14 | 157 | | |
| deionized water | 1855 | | |
| additive from Example 10 | 198 | | |
| | 2990 | | |

The panels received a coating by electrophoresis as described in Example 15. The deposition time on steel panels which had been subjected to pretreatment with zinc phosphate was 2 min 30 s.

EXAMPLE 19

A cationic electrodeposition bath containing the addition product from Example 11 was prepared by mixing the following ingredients.

| ingredient | parts by weight | solids | equivalents |
|---|---|---|---|
| resin for cationic electrodeposition from Example 2 | 790 | | |
| pigment paste from Example 14 | 157 | | |
| deionized water | 1855 | | |
| additive from Example 13 | 198 | | |
| | 2990 | | |

The panels received a coating by electrophoresis as described in Example 15. The deposition time was 2 min 30 s.

EXAMPLE 20

A cationic electrodeposition bath containing the addition product from Example 12 was prepared by mixing the following ingredients.

| ingredient | parts by weight | solids | equivalents |
|---|---|---|---|
| resin for cationic electrodeposition from Example 2 | 790 | | |
| pigment paste from Example 14 | 157 | | |
| deionized water | 1855 | | |
| additive from Example 12 | 198 | | |
| | 2990 | | |

EXAMPLE 21

A cationic electrodeposition bath containing the addition product from Example 13 was prepared by mixing the following ingredients.

| ingredient | parts by weight | solids | equivalents |
|---|---|---|---|
| resin for cationic electrodeposition from Example 2 | 790 | | |
| pigment paste from Example 14 | 157 | | |
| deionized water | 1855 | | |
| additive from Example 13 | 198 | | |
| | 2990 | | |

EXAMPLE 22

An additive-free cationic electrodeposition bath was prepared as a control from the mixture of the following ingredients.

| ingredient | parts by weight | solids | equivalents |
|---|---|---|---|
| resin for cationic electrodeposition from Example 3 | 1224 | | |
| pigment paste from Example 14 | 375 | | |
| deionized water | 1401 | | |
| | 3000 | | |

Panels precoated with iron/zinc alloy ('Galva-neal'), marketed by Advanced Coating Technologies Inc, under the name CHR HD6 60/Ad, were coated by electrophoresis under various voltages to evaluate the resistance of the film to microrupture (which is also described by the expression 'pinholes'). For all the panels coated under a voltage of 180 to 300 V, the bath temperature was 28° C., and the deposition time was adjusted to obtain a thickness of 21 μm. The results are given in Table 2.

EXAMPLE 23

A cationic electrodeposition bath containing the addition product from Example 8 was prepared by mixing the following ingredients.

| ingredient | parts by weight | solids | equivalents |
|---|---|---|---|
| resin for cationic electrodeposition from Example 3 | 1101 | | |
| pigment paste from Example 14 | 375 | | |
| deionized water | 1395 | | |
| additive from Example 8 | 129 | | |
| | 3000 | | |

The same panels as those defined in Example 22 were coated by electrophoresis following the procedure described in Example 15.

EXAMPLE 24

A cationic electrodeposition bath containing the addition product from Example 13 was prepared as a control by mixing the following ingredients.

| ingredient | parts by weight | solids | equivalents |
|---|---|---|---|
| resin for cationic electrodeposition from Example 3 | 1101 | | |
| pigment paste from Example 14 | 375 | | |
| deionized water | 1395 | | |
| additive from Example 13 | 129 | | |
| | 3000 | | |

TABLE 1

Surface appearance, adhesiveness and resistance to crater formation of cationic electrodeposition compositions

| | example | | | | | |
|---|---|---|---|---|---|---|
| | 15 | 16 | 17 | 18 | 19 | 20 |
| additive (ex No.) | none | none | 9 | 10 | 11 | 12 |
| property film thickness (μm) | 22 | 21 | 19 | 20 | 20 | 20 |
| oil spot resistance (1) | 5 | 5 | ≈2 | ≈2 | ≈2 | 3 |
| cross-hatching test of | 0 | 0 | 0 | 0 | 0 | 0 |

TABLE 1-continued

Surface appearance, adhesiveness and resistance to crater formation of cationic electrodeposition compositions

| | example | | | | | |
|---|---|---|---|---|---|---|
| | 15 | 16 | 17 | 18 | 19 | 20 |
| adhesiveness of topcoat (2) cross-hatching test of adhesiveness of topcoat after QCT (3) | 0 | 0 | 0 | 0 | 0 | 0 |
| surface appearance on ACT (4) | 5 | 5 | 0 | 0 | 0 | 0 |

(1) Oil spot resistance was assessed visually. A score was employed, ranging from 0 (perfect) to 5 (very poor) as a function of size, shape and appearance of the defects caused by drops of oil applied to a panel which had received a coating by electrophoresis, before the coating was baked.
(2) The topcoat is a conventional alkyd topcoat marketed by PPG Industries Inc, France, under the name 'leaf-Green'.
The cross-hatch test adhesiveness is determined by scribing a cross-hatch on the topcoat, producing tapes on the cross-hatched area, and pulling the tape at a 180 degree angle. Coatings that display good adhesiveness do not exhibit any peeling of the tape (score 0).
(3) The cross-hatch test adhesiveness is determined as described above, but after the panel which has received the topcoat has been treated in a condensation moisture chamber at 60° C. (QCT chamber) for 16 h.
(4) The ACT panels are those defined in Example 15.

TABLE 2

Surface appearance of panels precoated with iron/zinc alloy and coated with cataphoresis film

| | example No. | | |
|---|---|---|---|
| | 22 | 23 | 24 |
| | approximate number of pinholes counted over an area of 110 cm² for a film thickness of 18 to 21 μm | | |
| applied voltage | | | |
| additive | none | example 8 | example 13 |
| 180 V | 40 | 0 | 0 |
| 200 V | 1300 | 0 | 300 |
| 220 V | 1400 | 0 | 400 |
| 240 V | 1900 | 50 | 600 |
| 260 V | 2400 | 70 | 1300 |
| 280 V | 5400 | 700 | 2300 |
| 300 V | 5400 | 1300 | 5600 |

As may be seen from Table 1, according to the results of the tests performed with the compositions of the invention (Examples 17 to 20, with the respective additives from Examples 9 to 12):
the oil spot resistance is significantly improved,
the appearance of the topcoat is perfect, and craters are totally absent (score 0 on ACT).

These results are obtained without any loss of intercoat adhesiveness properties, as shown by the adhesiveness tests (scores 0). This is not the case if the product from Example 13 of the prior art is employed as additive.

Similarly, from Table 2 it can be seen that the use of an additive according to the invention (Example 8) makes if possible to work with application voltages of 220 V without the appearance of pinholes, which is not the case with the additive-free control or with the composition containing an additive of the prior art (Example 13).

What is claimed is:

1. An electrodepositable cationic paint composition comprising the reaction product of:
   (a) an amine-diol obtained from the reaction product of:
      (i) a primary amine of the formula $R-NH_2$ where R represents an aliphatic or aromatic radical, with
      (ii) at least one alkylene oxide comprising predominantly propylene oxide;
   (b) a polyfunctional material capable of reaction with hydroxyl group of said amine-diol.

2. The composition of claim 1 wherein the R group is alkyl and contains from 1 to 20 carbon atoms.

3. The composition of claim 1 wherein the R group is a linear or branched alkyl or aralkyl group.

4. The composition of claim 2 wherein the R group contains 1 to 12 carbon atoms.

5. The composition of claim 1 wherein the R group is selected from the group consisting of methyl, butyl or lauryl radicals.

6. The composition of claim 1 wherein the R group is aryl and contains from 6 to 18 carbon atoms.

7. The composition of claim 6 wherein the R group is phenyl.

8. The composition of claim 1 wherein the propylene oxide is present in amounts greater than 80 percent by weight based on total weight of alkylene oxide.

9. The composition of claim 1 wherein the amine-diol has a molecular weight of between approximately 800 and 1500.

10. The composition of claim 1 wherein the polyfunctional material is selected from the group consisting of isocyanates, acids and acid anhydrides.

11. The composition of claim 10 wherein the isocyanates are diisocyanates selected from the group consisting of toluene diisocyanate, isophorone diisocyanate, hexamethylene diisocyanate and tetramethylphenyl isocyanate.

12. The composition of claim 1 wherein the acids and acid anhydrides are diacids and diacid anhydrides selected from the group consisting of phthalic acid, maleic acid, phthalic anhydride and maleic anhydride.

13. The composition of claim 1 in which (b) is a polyfunctional isocyanate and in which the molar equivalent ratio of hydroxyl groups in (a) to isocyanate groups in (b) ranges approximately between 2/1 and 4/3.

14. The composition of claim 13 in which the molar equivalent ratio is approximately 3/2.

15. The composition of claim 1 in which (b) is a polyfunctional acid or acid anhydride and in which the molar equivalent ratio of hydroxyl groups in (a) to acid or anhydrides groups in (b) ranges approximately between 2/1 and 4/3.

16. The composition of claim 1 which also contains a grinding resin to facilitate dilution in water.

* * * * *